(12) United States Patent
Khatib

(10) Patent No.: US 9,976,182 B2
(45) Date of Patent: *May 22, 2018

(54) METHODS AND COMPOSITIONS FOR IMPROVED FERTILIZATION AND EMBRYONIC SURVIVAL

(71) Applicant: WISCONSIN ALUMNI RESEARCH FOUNDATION, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 66 days.

This patent is subject to a terminal disclaimer.

(21) Appl. No.: 14/736,298

(22) Filed: Jun. 11, 2015

(65) Prior Publication Data
US 2015/0292010 A1 Oct. 15, 2015

Related U.S. Application Data

(62) Division of application No. 12/882,213, filed on Sep. 15, 2010, now Pat. No. 9,080,212.

(51) Int. Cl.
C12Q 1/68 (2018.01)
C12P 19/34 (2006.01)

(52) U.S. Cl.
CPC ......... *C12Q 1/6881* (2013.01); *C12Q 1/6876* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS 9,080,212 B2 * 7/2015 Khatib ................ C12Q 1/6876

OTHER PUBLICATIONS

Zimin (Genome Biology, 2009, 10:R42, pp. 1-10).*
Khatib (BMC Genetics, 2009, 10:13, pp. 1-10).*

* cited by examiner

*Primary Examiner* — Sarae L Bausch
(74) *Attorney, Agent, or Firm* — Kening Li; Duane Morris LLP

(57) ABSTRACT

Single nucleotide polymorphic sites at positions 19069 and 25402 of the bovine STAT3 gene are associated with improved fertilization rate and/or improved embryo survival rate. The interactions between these two polymorphisms, and between them and the bovine STAT1 gene and fertilization and early embryonic survival rates were also disclosed. The interactions between STAT3 SNPs, and between STAT1 and STAT3 SNP19069 were highly significant for embryonic survival rate. Also disclosed are nucleic acid molecules, kits, methods of genotyping and marker assisted bovine breeding methods.

19 Claims, 4 Drawing Sheets

```
18061 acttttaaaa cagtactaaa ataatgttaa caagaaaaca ctgagaaatg gtgactatgt
18121 aaaaaatgaa atactcaaaa acagttaaag gacaaggaac atgctgggaa gaattttttct
18181 ggcgatgtca atgggatact ctgagttgca ggtaacagta gacctttaca gaaagcccag
18241 tgtggcttca gtaataagga aatttgcaac ccagtataac tggaaatgca gttagaacaa
18301 gttccggggtg gtgaaatcag tgactcaatt cctgtcacca aggatccaga accttccgtc
18361 tctcttctct gccaccataa gtagcacggg cattcgaggg ttccctctgg ttgcagcatg
18421 gttgcttgta gtaaaggcca cgtgtctcct tgctgatgtg cagctgaagc tacagaatgt
18481 aaatccagcc tgagggagaa ttccttcccc gtcggattga gacagtgtgg gtcctggcct
18541 cactcctgga ccaacactgt gcacatgtc ggttctgtgg gttagagca ggatccctg
18601 gaagtgggga tgggaaagat acttgctgga gtcaaggttc tgttaggaag aggggagtag
                      Primer Exon12F
18661 aggttgggta ggcaaccagc tgtgtcttct acttgagcat gtacagggat gttagatttc
18721 acgtatacca tgtaatcgag tcttgacag aaatcccag gagaacagca gttttccat
18781 ccgagtaaat gataggtgtt caaagtggac tttcaaagag actcggggcc tgttttatta
18841 acactggttt atattcttaa cagagactcc ggggacgttg cagctctcag agggtaagtt
18901 cagcatacag gcttccttct gttctgtata atctaacttt gtccctggcc attcggtcac
18961 gtatgtggtt ggtcttttcc tcctgtgatt caggtcccgg aaatttaaca ttctgggcac
19021 aaacacgaaa gtgatgaaca tggaagagtc taacaatggc agcctctcag cggagttcaa
19081 acacttggta catgggagaa gcctgggctc ccttctgca gggcctctgg cagggggagg
19141 gacttgggga gagccttacc tgacggagga tgctctttgt ttttcttaca gaccctgaga
19201 gagcagagat gcggtaatgg gggccgagcc aattgtgatg taagttttgt tggagatgat Primer Exon12R
19261 agctgagcag gagagaaaaa gagcctccat aagaacttcc ctagtggtta agactccacg
19321 cttccaatgc agggggtgtg ggtttgatcc ctggttagag aactaagatc tcacatgcct
19381 tgcagccaaa acactgaaac ttttttataaa agaaaagaa aaagagcctc cttactgccc
19441 agaagtagag cacctacct gctatttcag ctgcagtcac cgccagccaa cacatgagta
19501 gtcacacatg ccttggagga gttctctggc tcagcgcatt tccttgattg tccggagagt
19561 tagctcatct ttaaggagtg taaagtccct tgcccacacc catttggtag aaaaggagcc
19621 ttccgccttg cctgggactt tccaaattcc ccttctaact tctatgcact gacacggctt
19681 gtctcagctt ttggtgatct gttttggtca ctgaggtggg atgggtttca acacatccaa
19741 gttaaacatt ttaccaaaag agaaacagca aactctcttg ttctttaccc accttgtttc
19801 ttctctgtct cccattgact cagattcttg gattcttagt gttaagaata aacttaaggg
19861 aattccttgg tgattcagtg gttaagactc caggccttca ctgccatggg cctgggttca
19921 attcctggtt gggaaactaa gattccacaa actatatggc cccccaaaaa agaataaact
19981 ttaaaaaga gaaagtatat gtgaccaagc actggttta aatctttttt ataaaattgt
20041 gacaccctat tcttttctg tttgtctcct gagccgttct tacccctctc tctagaatgt
20101 agcaggcctt ttaaaaaaac aaactgaatc tataagactt gacagcagtt aaagagtgag
20161 gttgtttcta tgcagtgata tgggaagatg tatgtggcat atttattgag aaaaaaatgc
20221 aaagtaattt gagtagtata ctagtataat tgttttaaaa tttactgttt tttctccatt
20281 catgtctgca ttacaaaatt ctagaggaat gtctaccaaa tagtgcttat atatttgtgc
20341 tgctgttctc acccaaagct actctatact atctctgtaa tatttgcatt taaaattgaa
20401 tgtgtatttc ttttgtttatg agagaacatt ttaaaatatg agttggaatt tctaataatt
20461 cattgacagt tctcattcaa aatagtcgct atgttgctgg tgtatcaatt gttataatca
20521 ctttgaaaaa cagttgggca ttatgaaaat aaatatacc tatataccag cagtgccact
20581 ctcgggattt aacaatagag aaatctttgc tcataggtgc caggagactg gcgccaggag
20641 acatgcattt catgtcccaa cagcctaatt gtaaggccta aatacaaccc atatgtcaac
20701 agcactagag tggataaatg atctgtggta tagtcaggtg atggaatact atacagctat
20761 gaagatgtat aaattgcagg tatacacaat tacataggtg tgaaaagcga gtcacagtat
20821 gagattcaca acccccaccc caattaaac aacacataca ttgtttagag atataaatgc
20881 aggaaaacca taagaaggg ctaggaaatg acaaactcaa agacaaaat agcagtcact
20941 tctgaggtag gaggctcagg gatggatgga gttgggaagg ggaccggag aacctccatg
21001 gtgacggtct ctgccttaca ctgagggggtg ggtaacagag tgttcagtgt tttgccatta
21061 tgctgtttcc atttttatcca tgaccaactg gatctccata gtatcataat aaagccgata
21121 agaggtcagg ttgtagatca gagcactgga gagtcgtaga gttggaaaga ccatgtgctc
21181 cagttgtatc catggccacc tggtgcgttg cgcttcagga tggtgtagtg atggctgtca
21241 ggactcagtg ccatcctctc tgaggaagag catccttctc attctcgtag gcctccctga
21301 ttgtgaccga ggagctgcac ctgatcacct ttgagactga ggtgtatcac caaggcctca
```

Figure 1

```
21361 agattgacct ggaggtgagt tctgcacaga actgggtaga accgcctgca ggatgattca
21421 gaatgggget tcttctagtc agggttttca ctctagaagg tggaatgatg actctttact
21481 cagcactgtg tttacatttg cttcttttc tccaaaaatt tgttagtatc ttgcctgagt
21541 gcttagaaga tacatgtcta ctcaggttcc agcgaacttg atgtaaaaac tcgtatttag
21601 gaattaatta tagccaactt tatacagttt ggacaaaaca gtctttcaac caccaccgtt
21661 tttagtatcc aaacaatcat ggcatttacc tgctcttcc ccaactttct tgattttaaa
21721 ttaaagatac acctgaaaaa gcaagcaccc tagtctttga ttcctgggac ctctctatta
21781 aatgggcaga tacagcttca atgcagcaat gcgggagact tgggttcgac ttccctgggt
21841 tggaaagatc ccctggagaa gggaaaggct acccactcca gtatcctggc ctggagaatt
21901 ccacggactg tataggccat gggtcgcag agttggacac aactgagcaa cttgcattct
21961 tttcacagct tcaattcgtg aaagtcttcc aagttttata aatggggagt ccgtggactg
22021 tgagtccact gtgaggagtc agctttgtaa attcctggtg atactcagac agcccctgag
22081 ttcagcctac tctccacgct gggtgtcaag ctgaccgggc cccacagctt cctgagggtt
22141 ggcagcaagt gtactccacg acctctcctt ttattctgaa ccctgcgaga tgcgggtgaa
22201 gaggtttctg gagcctcaag ggccctctgc ctccccagct cattcccgc tcctccaca
22261 gacccactcc ttgccagtgg tggtgatctc caacatctgt cagatgccca atgcctgggc
22321 gtccatccta tggtacaaca tgctgaccaa caacccaag gtgagttgga ggcccggtt
22381 ctccggaggc tccttggtgc ctcggggctg ccgcccagca ggcgccaccc tctcatctaa
22441 aggagcaaat gtgtcatttc caatagaacg tgaactttt caccaaaccc ccgatcggaa
22501 cgtgggatca agtggccgag gtgctgagct ggcagttctc ctctaccacc aagcgcgggc
22561 tgagcatcga gcagttgacg acgctggcgg agaaactctt aggtcagccc ttgacctctt
22621 ctccctttgc tgtccttgca aaaggaatct ggcccatggg gttgttcgtt gaggaaagtt
22681 gactgagcaa ggcgctgggc agaatacacg tgctccagca ggccctgaaa tcgggacgca
22741 gaggaggttt gcgcctgtga tcacttttat gagacgggag gcagatttct tctgttggtg
22801 gctgtctccc tgggtacttt gtccagcctt aggaaagtat tttaaatgta tgttcgagct
22861 aaaggcttgg catccctgtc tgttttttca agaaaatgta gcttgtttt aattttttt
22921 cctggaagaa aaaagtctta gaatgtttta cgtgccgtct agctttgtcc tgtgctgcca
22981 tgaaacatgg gctctccggg tgcctcagtg gtagagaatc cacctgccag tgcaggagac
23041 ttggatttga cccttgggtc aggaagatcc cctggaggag gaaatgataa cccactccag
23101 tattcttgcc tgggaaatcc caaggagagg aacttggtag ggctgcagtc agacatgact
23161 gacggactga ccatgcatga ctaaacgtga ccctgtaact caagctgtca gcttcttagt
23221 gtgttctgct gatcccgaga ctgccacacg aggctagaaa gggcagcagg gacttgatac
23281 atcaccccacc acctccgcta aacaacaact taggggcat caaacgatgg gattgggtgg
23341 tggggagggg tgcgtatgta tgcacacaag agtgccaacg ttcaagtgca tgaaaaccaa
23401 gtttcgggc gtgttgtggg acaactgtct gtctgtctgt ttgaagaaag atctggattt
23461 aaaactgcaa attatatgac ttttttttt ctttcaggac ctggtgtgaa ctattcaggg
23521 tgtcagatca catgggctaa attttgcaaa gtaagccacc gtgtgaactc catccatgag
23581 gctgcctcat agaggagga ggggcaggg acattagct gtgggatgt cgtggaggc
23641 agtgggcctg aaggccccgg actcttggtc tggcggccaa gatgacctgc ctgagggtag
23701 atgggcttga ggattttggt ggcacctcac cccttaaag gaagagccca gggaggtggg
23761 ggactgacct ttcccattac tcttttctcc aggaaaacat ggctggcaag ggcttctcct
23821 tctgggtctg gctggacaac atcattgacc tggtgaaaaa gtacatcctg gcctttgga
23881 acgaagggta ggttggaact cttgtgtctg acagaacaca caggggtgac aagtcgccta
23941 ctctccagcc aggttggctg caacacagag gtccctcagc cccaaccttg ctgttgctcc
24001 tctctgtctc caggtatata atgggcttca tcagcaagga gaggggaacgg gccatcttga
24061 gcactaagcc cccagtacc ttcctgctga gattcagtga aagcagcaaa gaaggaggcg
24121 tcacctcac ctgggtgag aaggacatca gcggtaagct tagtgattcc ccaccgcaac
24181 ttgtggccag cactgctgtg gctggccatg gctgctgcta gttcaggca cctgctgcc
24241 ccttgtgggc agggatggcc tcgcattctc ctgcctcaga cttggaaggt acccggtgat
24301 cattttatg agatgggaag acttggcttc tctaaattct tccagctgga ggattggttt
24361 gccagtttta ttttgctccc tgcaagggt taatcagttc agtcgctcag tcgtgtccga
24421 ctctttgtga ccctatgagt cacagcacgc caggcctccc tgtcatcacc aactcccaga
24481 gttcactcaa actcatgtcc atcgagtcag tgatgtcatc cagccatctc atcctctgtc
24541 gtcccttct cctcctgccc ccaatccctc ccagcatcag ggtctttcc aatgagtcaa
24601 ctctttgcat gaggtggcca aagtaatgga gtttcagctt tagcatcagt ccttccaatg
24661 aacaccagg actgatctcc tttaggatgg actggttgga cctccttgca gtccaaggga
```

Figure 1 (cont'd)

```
24721 ctctcaagag tctttctcca taccacagtt caaaagtatc aattctttgg cgctcagctt
24781 tcttcacagt ccaactctcg catccataca tgaccactgg aaaaaccata tccttgacta
24841 gacggacctt tgttggcaaa gtaatgtctc tgcttttgag tatgctatct aggttggtca
24901 taactttcct tccaaggagt aagcgtcttt taatttcatg gctgcagtca ccatctgcag
24961 tgattttgag ccccccaaaa taaagtctga cactgtttcc actgctgccc catctatttg
25021 ccatgaagtg atgggaccgg atgccatgat cttcattttc tgaatgttga gctttaagcc
25081 aacttttca ctctcctctt tcactttctt caagaggcta atatttgcct agaaattggt
25141 aattttttt tttgaaattt gaaatttaaa ttgtattctt catctcsttt cttacccact
                                     Primer Intron19F
25201 ctgttcatat atcttataaa agtaattatt caactatgtt acttgtggcc cagctgaata
25261 gcttctcccg aagcctgctg aacatttcca tagtaccaga caactgggca gaatattcag
25321 ggtctcgaac actaggttgg cataagcctt tcccctcaa gggaaaatca atcaggtagt
25381 cttctctaag atcacccgag tattctcttt ctgtatccca tgacaggcaa gacccagatc
25441 cagtcagtgg aaccttacac caagcagcag ctgaacaaca tgtcatttgc tgaaataatc
25501 atgggctata agatcatgga tgccaccaat atcctggtgt ctccactggt ctatctctac
25561 cccgacattc caaggagga cgcgttcgga aagtactgtc ggcggagag ccaggagcat
25621 cctgaagccg accaggtag ttgttgattt tccgcaacag ccacttggtt ctggggagaa
                                                    Primer Intron19R
25681 gtgggaaatc gtaggatcct tggggacag gtaaggtaaa tgcctggaga gcctggtgat
25741 ctgttttttt ctttctttct ttttaagaaa ttttctcttt ataatttta tttattatt
25801 tttgtttttg gctgtgctgg gtcttcattg ccgtatgggc ttttctgtag ttggggcaag
25861 cggggctat gctctacttg cagtgcgtgg gcttctcatt gcggtggctt ctcttgttgc
25921 agagcttggg ctctaggcac agactcagt agttgcggca ggtgggctca gtagttgcag
25981 ttccaaggct ctagagccac aggctcaatg gttgtggcac acgggcttag ttactccgag
26041 gcatatggag tcttctcgga ccagggatca aacctgtgtc tcctgcgttg gcaggcaaat
26101 tctttaccac cgagatatcc aggaaagccc agtctggtga tctttattcc tcttctggg
26161 aaagaactta atagtgagtg cctttagggg caattgatgg ggttagagag aggagaggaa
26221 tcagtcacca ggctctgccc cactggaggc accggtctaa agggaaaac agctcacaca
26281 tacccagaca tacctaagac actacgaaga gaaaccgagg gcggaattct ctagaaacag
26341 gatgccagc cagcacagca cttcttgcaa agcatatgct ggaaggtttg cgactcagac
26401 ttcagtctag agtgtttcct ttccccatca ttgaacaatg taagcagccc aagtgggatg
```

Figure 1 (cont'd)

```
1    ctttaaatat  agcctcaagt  ttgccagtgg  cttgcctgtg  aaatagtgca  aagctgtcct
61   gtatctgggc  agaggataaa  agttatgtgt  gttattatat  tttccacact  ggccattgaa
121  aactaaagat  tctctttctt  gggagaatta  gcttttggta  tggctttatg  atgctggcta
181  atatcaatag  aaggaagtaa  actttacaaa  ttcatgagta  gtatcttcca  tttcagcttt
241  aataccaaag  ttgaatatat  tctgccttca  tcatgaaatt  gaagttagta  aatgaaactg
301  tcttcacagt  tctatcaagg  gagccaaact  attaacagct  ctcttaaggc  aaatcctatt
361  attttttcaa  aaagttgaaa  ttaattgtag  atgtaaacaa  actcagaaat  ttaatgcatg
421  tttcataagt  gggttcactt  gtctttattg  tttagtaaaa  attttaaaat  tgagaagaaa
481  aactagtaat  tgacaaatca  ttaggtggag  attatgagaa  tccaataatt  tgaaaactca
541  tcctgtgtaa  ctgccttgag  aattgggtaa  ttttcactgg  caaatgtgta  tctctcacaa
601  atacattaca  gatggttcca  ctaaaa
```

Figure 2 (prior art)

METHODS AND COMPOSITIONS FOR IMPROVED FERTILIZATION AND EMBRYONIC SURVIVAL

CROSS REFERENCE TO RELATED APPLICATIONS

This is a divisional application of U.S. application Ser. No. 12/882,213 filed on Sep. 15, 2010, claiming priority to U.S. patent application 61/242,390, filed on Sep. 15, 2009, the entire disclosure of which is incorporated herein by reference.

STATEMENT OF GOVERNMENT INTEREST

This invention was made with government support under 09-CRHF-0-6055 awarded by the USDA/NIFA. The government has certain rights in the invention.

FIELD OF THE INVENTION

The present invention relates to a method of genetic testing for improved fertilization rate and embryonic survival rate in animals, especially dairy cattle.

BACKGROUND OF THE INVENTION

Dairy cows are significant investments for dairy farmers, yet infertility is a major cause of dairy cow culling and economic loss. Enormous efforts, such as animal breeding and artificial insemination, have been and continue to be invested in ensuring improved breeding programs. The decline in reproductive performance in high-producing dairy cows is a major concern of farmers worldwide (Royal et al., 2000; Dobson et al., 2008). Major factors contributing to this poor performance in dairy cattle are low fertilization rate and early embryonic loss (Santos et al., 2004; Morris and Diskin, 2008). Although genetics account for about one-third of the decline in pregnancy rate of dairy cows (Shook, 2006), the identification of major genes affecting cow fertility has been challenging, probably due to the low accuracy of fertility data collected in the field and to the low heritability of this trait. The heritability of open days and pregnancy rate is about 0.04 (VanRaden et al., 2004).

Typically, artificial insemination in dairy cattle is successful only 30-35% of the time. The reasons for this are not clear. However, it is understood that both biological and environmental factors affect fertility rate. Some environmental factors such as heat, lack of precipitation, and other factors can cause stress in cattle and can drop the fertility rate to 10-15%. Commercial artificial insemination operations often shut down in July and August due to the drop in fertility caused by the hot, dry weather. It is also known that certain bulls are more fertile than others due to their genetic makeup. Identifying highly fertile bulls, however, is a time-consuming and expensive process. It can take 5-10 years of tracking the attempts of artificial insemination using semen from a bull before it can be certified as a quality bull.

Marker-assisted selection, on the other hand, can lower the high cost and reduce the extended time commitment of progeny testing currently used to improve sires, since young bull progeny could be evaluated immediately after birth or even prior to birth for the presence/absence of the marker, and young bulls that are determined by genetic testing to have undesirable markers would never be progeny tested.

There is thus a need for a method of genetically evaluating the bulls, as well as the cows, e.g., by genetic testing, to enable a quick and accurate evaluation of its fertility as well as the survival rate of embryos conceived therefrom.

Signal transducer and activator of transcription (STAT) proteins are a family of 7 structurally and functionally related proteins: STAT1, STAT2, STAT3, STAT4, STAT5A, STAT5B, and STAT6 (Darnell, 1997). The STAT proteins are transcription factors that play important roles in cytokine signaling pathways (Kisseleva et al., 2002). Following their phosphorylation by janus-kinases (JAKs), STATs translocate to the nucleus to regulate transcription of different genes. The JAK/STAT pathway was found to be conserved in vertebrates (Hombría and Brown, 2002). Recent studies have shown that STAT proteins are involved in the fertilization process and in early embryonic development (Maj and Chelmonska-Soyta, 2007). Teglund et al. (1998) showed that disruption of the Stat5 gene leads to infertility in female mice as a result of small-sized or absent corpora lutea. Truchet et al. (2004) reported that Stat1 and Stat3 are expressed in mouse oocytes and preimplantation embryos and concluded that these 2 genes might have functional importance in early embryonic development because of their roles in the cell cycle and apoptosis. Takeda et al. (1997) reported that Stat3-deficient mice die before embryonic day 8.5 and concluded that Stat3 is an essential gene for early embryonic survival and that its deficiency cannot be compensated for by other STAT proteins. Khatib et al. (2008a, 2009) showed that the CC genotype in exon 8 of bovine STAT5A was associated with high fertilization and early embryonic survival rates.

Given that several genes of the JAK/STAT pathway have been found to be associated with fertility traits in cattle, STAT1 and STAT3—also members of this pathway—were chosen as candidate genes for fertilization rate and early embryonic survival in cattle. Previously, the present inventor has disclosed that single nucleotide polymorphisms (SNPs) in the STAT5A gene are associated with both milk production and fertility (U.S. patent application Ser. No. 12/267,076), and a SNP in the coding region of STAT1 gene is associated with increased milk yield, milk fat and protein percentages (U.S. patent application Ser. No. 11/624,053).

Interestingly, after their phosphorylation in the cytoplasm by the JAKs, STAT1 and STAT3 interact with each other by forming a heterodimer complex which translocates to the nucleus and binds specific DNA sequences (Kodama et al., 1997).

In order to overcome these challenges, the present inventor has constructed an in-vitro fertilization (IVF) system which has the advantages of a unified environment and well-isolated components of the embryonic development process. Indeed, using this system, SNPs in several genes and interactions between them have been found to be associated with fertilization and early embryonic survival rates (Khatib et al., 2008a,b; Khatib et al., 2009). There remains, however, a need to determine the single gene effects of STAT1 and STAT3 polymorphisms and their interactions on fertilization and embryonic survival rates.

SUMMARY OF THE INVENTION

The present inventor investigated the effects of the interactions between polymorphisms in the bovine STAT1 and STAT3 genes and fertilization and early embryonic survival rates using an in-vitro fertilization system. Two SNPs, SNP25402 and SNP19069, were identified in the STAT3 gene, and single SNP analysis revealed significant association between SNP25402 and fertilization rate. The interactions between these two STAT3 SNPs and between a previously-identified STAT1 SNP, SNP213, and SNP19069 were highly significant for embryonic survival rate.

Accordingly, the present invention provides an isolated nucleic acid molecule comprising at least one polymorphic site selected from the group consisting of position 19069 and position 25402 of SEQ ID NO: 1 (part of the bovine STAT3 gene), and at least 8, 9, 10, 11, 12, 13, 14, 15, 16 or 17 contiguous nucleotides (nt) or bases of SEQ ID NO: 1 adjacent to the polymorphic site, wherein the nucleic acid molecule comprises an adenine at the polymorphic position. It is recognized that SEQ ID NO: 1 is already known, and the nucleic acid molecule therefore does not encompass one that consists of SEQ ID NO: 1.

Preferably, the nucleic acid molecule which comprises at least 15, more preferably at least 20, still more preferably at least 25, contiguous bases of SEQ ID NO: 1 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt, preferably not more than 100 nt, still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

In another embodiment, the nucleic acid molecule contains the polymorphic site which is at the 5'-ed of the nucleic acid molecule.

The present invention also provides an array of nucleic acid molecules comprising at least two nucleic acid molecules described above.

The present invention further provides a kit comprising a nucleic acid molecule described above, and a suitable container.

Also provided is a method for detecting single nucleotide polymorphism (SNP) in bovine STAT3 gene, wherein the STAT3 gene has a nucleic acid sequence of SEQ ID NO: 1, the method comprising determining the identity of a nucleotide at one or both positions 19069 and 25402, and comparing the identity to the nucleotide identity at a corresponding position of SEQ ID NO: 1.

In another embodiment, the present invention provides a method for genotyping a bovine cell, using the method above. Suitable bovine cell may be an adult cell, an embryo cell, a sperm, an egg, a fertilized egg, or a zygote. The identity of the nucleotide may be determined by sequencing the STAT3 gene, or a relevant fragment thereof, isolated from the cell.

In a further embodiment, the present invention provides a method for testing the fertility of a bull cattle, the method comprising collecting a nucleic acid sample from the cattle, and genotyping said nucleic sample as described above, wherein a bull having a STAT3 gene sequence which comprises an adenine at positions 19069 or 25402, or both is selected for breeding purposes.

Preferably, a bull having a STAT3 gene sequence which is homozygously A at one of the above described polymorphic sites is selected for breeding purposes.

Preferably, a bull having a STAT3 gene sequence which is homozygously A at both of the above described polymorphic sites is selected for breeding purposes.

Further provided is a method for selectively breeding cattle using a multiple ovulation and embryo transfer procedure (MOET), the method comprising superovulating female animal, collecting eggs from said superovulated female, in vitro fertilizing said eggs using semen from a suitable male animal, implanting said fertilized eggs into one or more other females allowing for an embryo to develop, genotyping the developing embryo, and terminating pregnancy if the developing embryo does not have adenine (A) at position 19069 or 25402. Preferably, pregnancy is terminated if the embryo is not A at positions 19069 and 25402.

In a preferred embodiment, the present invention provides a method for selectively breeding dairy cattle, comprising selecting a bull whose STAT3 gene is hemizygously or homozygously adenine at position 19069 or 25402, and using its semen for fertilizing a female animal. Preferably the bull is homozygous with regard to the above SNP site. More preferably, the female animal is also homozygous at the above SNP site.

In another preferred embodiment, the present invention provides a method for testing the fertility of a cattle, the method comprising collecting a nucleic acid sample from the cattle, and genotyping said nucleic sample as described above, wherein a cattle having a STAT3 SNP and a STAT1 SNP213 (FIG. 2; SEQ ID NO: 2) combination described below is selected for breeding purposes.

In a preferred embodiment, selection of animals for breeding purpose is based on the interactions between the various SNP genotypes. In general, based on the results shown in Table 3 below, a bull or a cow which is homozygously GG at SNP19069 and homozygously AA at SNP25402 (designated as "SNP19069/SNP25402=GG/AA") should not be selected for breeding purposes, and pregnancies with such a genotype should be terminated. On the other hand, a bull or a cow which is homozygously AA at SNP19069 and homozygously CC at SNP25402 (designated as "SNP19069/SNP25402=AA/CC") is selected for breeding purposes. A bull or a cow which is homozygously AA at SNP 19069 and heterozygously AC at SNP25402 (designated as "SNP19069/SNP25402=AA/AC") can also be selected for breeding purposes. Likewise, a bull or a cow which is homozygously GG at SNP 19069 and homozygously CC at SNP25402 (designated as "SNP19069/SNP25402=GG/CC") can be selected for breeding purposes; a bull or a cow which is heterozygously AG at SNP19069 and homozygously CC at SNP25402 (designated as "SNP19069/SNP25402=AG/CC") can also be selected for breeding purposes; a bull or a cow which is heterozygously AG at SNP19069 and homozygously AC at SNP25402 (designated as "SNP19069/SNP25402=AG/AC") can be selected for breeding purposes; a bull or a cow which is homozygously AA both at SNP19069 and SNP25402 (designated as "SNP19069/SNP25402=AA/AA") can be selected for breeding purposes; a bull or a cow which is homozygously GG at SNP19069 and heterozygously AC at SNP25402 (designated as "SNP19069/SNP25402=GG/AC") can be selected for breeding purposes; and a bull or a cow which is heterozygously AG at SNP 19069 and heterozygously AC at SNP25402 (designated as "SNP19069/SNP25402=AG/AC") can be selected for breeding purposes. In other words, any one of the following genotypes or STAT3 SNP combinations may be selected for breeding purposes: SNP19069/SNP25402=AA/CC; SNP19069/

SNP25402=AA/AC; SNP19069/SNP25402=GG/CC; SNP19069/SNP25402=AG/CC; SNP19069/SNP25402=AG/AA; SNP19069/SNP25402=AA/AA; SNP19069/SNP25402=GG/AC; and SNP19069/SNP25402=AG/AC.

Based on the results shown in Table 4 below, a bull or a cow which is homozygously GG at the SNP19069 and homozygously TT at STAT1 SNP (designated as "SNP19069/STAT1 SNP=GG/TT") should not be selected for breeding purposes, and pregnancies with such a genotype should be terminated. On the other hand, a bull or a cow which is homozygously AA at SNP19069 and homozygously TT at STAT1 SNP (designated as "SNP19069/STAT1 SNP=AA/TT") is selected for breeding purposes. A bull or a cow which is heterozygously AG at SNP19069 and homozygously TT at STAT1 SNP (designated as "SNP19069/STAT1 SNP=AG/TT") can also be selected for breeding purposes. Likewise, a bull or a cow which is homozygously GG at SNP 19069 and homozygously CC at STAT1 SNP (designated as "SNP19069/STAT1 SNP=GG/CC") can be selected for breeding purposes; a bull or a cow which is homozygously AA at SNP 19069 and heterozygously CT at STAT1 SNP9 (designated as "SNP19069/STAT1 SNP=AA/CT") can be selected for breeding purposes; a bull or a cow which is heterozygous AG at SNP19069 and heterozygously CT at STAT1 SNP (designated as "SNP19069/STAT1 SNP=AG/CT") can be selected for breeding purposes; a bull or a cow which is homozygously AA at SNP19069 and homozygously CC at STAT1 SNP (designated as "SNP19069/STAT1 SNP=AA/CC") can be selected for breeding purposes; a bull or a cow which is heterozygously AG at SNP19069 and homozygously CC at STAT1 SNP (designated as "SNP19069/STAT1 SNP=AG/CC") can be selected for breeding purposes; and a bull or a cow which is homozygously GG at SNP19069 and heterozygously CT at STAT1 SNP (designated as "SNP19069/STAT1 SNP=GG/CT") can be selected for breeding purposes. In other words, any one of the following genotypes or SNP19069/STAT1 SNP combinations may be selected for breeding purposes: SNP19069/STAT1 SNP=AA/TT; SNP 19069/STAT1 SNP=AG/TT; SNP 19069/STAT1 SNP=GG/CC; SNP19069/STAT1 SNP=AA/CT; SNP19069/STAT1 SNP=AG/CT; SNP19069/STAT1 SNP=AA/CC; SNP19069/STAT1 SNP=AG/CC; and SNP19069/STAT1 SNP=CT/GG.

In a preferred embodiment, a method for genotyping a bovine cell is provided, the method comprising obtaining a nucleic acid sample from said cell and determining the identity of a nucleotide of at least one position selected from the group consisting of position 19069 of the bovine STAT3 gene and position 25402 of the bovine STAT3 gene. Preferably, the identity of the nucleotides at both positions is determined. Preferably, the method further comprises determining the identity of a nucleotide of position 213 of the bovine STAT1 gene.

A method for selectively breeding cattle is further provided, wherein the method comprises testing an animal as described above, and selecting the animal as a breeding parent only if the animal comprises a SNP combination selected from the group consisting of SNP 19069/STAT1 SNP=AA/TT; SNP 19069/STAT1 SNP=AG/TT; SNP 19069/STAT1 SNP=GG/CC; SNP19069/STAT SNP=AA/CT; SNP19069/STAT1 SNP=AG/CT; SNP19069/STAT1 SNP=AA/CC; SNP19069/STAT SNP=AG/CC; SNP19069/STAT1 SNP=CT/GG; SNP19069/SNP25402=AA/CC; SNP19069/SNP25402=AA/AC; SNP19069/SNP25402=GG/CC; SNP19069/SNP25402=AG/CC; SNP19069/SNP25402=AG/AA; SNP19069/SNP25402=AA/AA; SNP19069/SNP25402=GG/AC; and SNP19069/SNP25402=AG/AC.

DESCRIPTION OF THE DRAWINGS

FIG. 1 shows a portion of the STAT3 gene sequence (SEQ ID NO: 1) where the two polymorphic sites are shown.

FIG. 2 shows a portion of the STAT1 gene sequence (SEQ ID NO: 2) where the polymorphic site is shown.

DETAILED DESCRIPTION OF THE INVENTION

Two positions of the bovine STAT3 gene are found to be polymorphic. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNPs are used for determining the genotypes of the STAT3 and STAT1 genes, which are found to have strong correlation to fertilization rate and embryonic survival.

The provided sequences also encompass the complementary sequence corresponding to any of the provided polymorphisms. In order to provide an unambiguous identification of the specific site of a polymorphism, the numbering of the original STAT3 sequence in the GenBank is shown in FIG. 1 and is used throughout this disclosure.

The present invention provides nucleic acid based genetic markers for identifying bovine animals with superior breeding (such as fertility and embryo survival rates) traits. In general, for use as markers, nucleic acid fragments, preferably DNA fragments, may be as short as 7 nucleotides (nt), but may preferably at least 12 nt, 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid. segment (or nucleotide analog segment) which can be used to identify by hybridizing to a specific polynucleotide sequence present in samples, said nucleic acid segment comprising a. nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or C. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the STAT3 gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of position 25402 may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the E. coli mutS protein (Modrich, P. Ann Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the STAT3 gene of the sample of interest may be amplified via PCR and directly sequenced, and the sequence be compared to the wild type sequence shown in FIG. 1. It is readily recognized that, other than those specifically disclosed herein, numerous primers can be devised to achieve the objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved. fertilization rate and embryonic survival.

Further provided is a method for genotyping the bovine STAT3 gene, comprising determining for the two copies of the STAT3 gene present the identity of the nucleotide pair at positions 25402 and 19069.

One embodiment of a genotyping method of the invention involves examining both copies of the STAT3 gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

In previous studies, the present inventor demonstrated the ability of the IVF system to identify associations between candidate genes and fertility traits (Khatib et al., 2008a,b; Khatib et al., 2009). Here, the association was investigated of single gene and SNP-SNP interactions of STAT1 and STAT3 polymorphisms with fertilization rate and early embryonic survival using the IVF system. Truchet et al. (2004) hypothesized that because of the roles of STAT1 and STAT3 in the control of cell cycle and apoptosis, these two genes might have important roles in the early embryonic developmental stages. Indeed, the results disclosed herein show that single gene analyses revealed significant associations of STAT3 SNP25402 and STAT1 SNP213 with fertilization rate. Also, STAT3 SNP19069 was found to be associated with early embryonic survival. Moderate association was found of SNP 19069 with fertilization and survival rates and of STAT1 SNP213 with fertilization rate.

Given that STAT1 and STAT3 proteins interact biologically by forming a heterodimer and translocating from the cytoplasm to the nucleus (Kodama et al., 1997), the present inventor also investigated the effects of the SNP-SNP interactions of these genes on fertility traits. The results showed highly significant association of STAT3 SNPs (SNP19609/SNP25402; P=3.690E-06) and of STAT1/STAT3 SNPs (STAT1/SNP19069; P=0.422E-06) with early embryonic survival. Given that single SNP analysis of STAT1 and STAT3 SNP25402 did not reveal highly significant associations with survival rate, these results testify to the merit of including epistsatic interactions in association studies (Carlborg and Haley, 2004).

For the significant interactions associated with survival rate, the observed survival rate for genotype combinations was calculated. For STAT3 SNP, the survival rates of embryos produced from AA/GG and that of CC/AA ovaries was extremely different than all other genotype combination. Likewise, for STAT1/SNP19069 the survival rate of embryos produced from TT/AA ovaries was relatively high compared to other genotype combinations. One can argue that the number of embryos carrying these genotypes is relatively small (Tables 3 and 4). Nevertheless for STAT3 SNPs, the difference between the second highest genotype combination (AC/AA) and the second lowest (AC/AG) observed survival rate was 8.7% (Table 3). For STAT1 SNP213/SNP19069 interaction, the difference between the second highest (TT/AG) and the lowest (TT/GG) observed survival rate for genotype combinations was 12.6% (Table 4). These differences in survival rate could not be observed in the single SNP analysis.

In a previous study, we reported that some genes in the POU1F1 pathway did not show significant associations with fertility traits using single gene analysis whereas gene-gene interactions were significant (Khatib et al., 2009). Thus, genotype combinations found to be associated with high embryonic survival rate in this study could be employed in gene-assisted selection programs aimed at improving fertility performance in dairy cattle.

STAT1 and STAT3 are members of the JAK/STAT signaling pathway. Truchet et al. (2004) reported that that STAT1 and STAT3 are present in mouse oocytes and in preimplantation embryos and that JAK/STAT pathway is functional during early embryonic development. Furthermore, in previous studies, we reported the several members of the JAK/STAT pathway were found to be associated with early embryonic survival in cattle. Taken together, our results provide additional support for the genetic involvement of JAK/STAT pathway in the early survival of cattle embryos.

In another embodiment, the present invention provides novel cattle genotyping, selective cattle breeding and related methods, based on the discovery that the above described STAT3 polymorphisms, in combination with a certain polymorphic form of the STAT1 gene, confers highly desirable fertilization and embryonic survival rate to cattle. The STAT1 polymorph, hereinafter referred to STAT1 SNP213, is depicted in FIG. 2, and was previously disclosed in U.S. patent application Ser. No. 11/179,581, the entire content of which is incorporated herein by reference. All the above description with regard to the SNPs in the STAT3 gene, including the terminology, the techniques and method of using, are equally applicable to STAT1 and the STAT1 SNP213.

The following examples are intended to illustrate preferred embodiments of the invention and should not be interpreted to limit the scope of the invention as defined in the claims.

EXAMPLES

Materials and Methods

In-Vitro Fertilization and Embryo Production

Ovaries from mature Holstein cows (n=512) were collected from a local abattoir over a 3 yr period and immediately used in the IVF experiments. No genetic relationship information was available for these cows. Oocytes were aspirated from antral follicles and immediately incubated in maturation medium. On average, about 16.8 oocytes were aspirated from each ovary. Ovaries (n=67) from which fewer than 4 oocytes were harvested were excluded from the analysis. All oocytes aspirated from an ovary were combined with semen from one bull for an incubation period of 18-25 h as described in Khatib et al. (2008a,b). Semen of unrelated bulls (n=12) was purchased from different artificial insemination companies in Wisconsin. Fertilization rate was calculated as the number of cleaved embryos at 2 d post-fertilization out of the total number of oocytes exposed to sperm. After the fertilization period (fertilization=day 0), putative zygotes were stripped of their cumulus cells by vortexing and cultured until d 7. The first morphological evaluation of embryos was done on d 5 of culture. On d 5, embryos were evaluated for evidence of compaction or cell coalescence. Embryos undergoing compaction at this point will typically have 32-64 cells. On d 7 of culture, embryos previously classified as morulas (compacted) were re-evaluated for the presence of a blastocoele, whose presence classifies an embryo as a blastocyst. Survival rate of embryos was calculated as the number of normally developed blastocysts on d 7 out of the total number of embryos cultured.

Standard error mean (SEM) of fertilization or survival rate was calculated by $\sqrt{\hat{p}(1-\hat{p})/n}$ where n was sample size and $\hat{p}$ was fertilization or survival rate. A total of 7,519 oocytes were exposed to sperm, and a total of 5,075 embryos were produced.

Genotyping

DNA was extracted from ovaries (n=445) and semen samples (n=12) using standard phenol/chloroform protocols. The DNA concentrations were measured using a spectrophotometer (Ultraspec 2100; Amersham Biosciences). Three DNA pools were constructed from 50 different ovary samples to contain 50 ng of DNA from each sample and amplified with different sets of primers designed from the STAT3 gene, which is located on chromosome 19.

Amplification and SNP identification were as described in Khatib et al. (2008a,b). An A/G SNP was identified in exon 12 at position 19069 and an A/C SNP was identified in intron 19 at position 25402 (GenBank accession no. NC 007314; region 43752931 to 43784155). For genotyping SNP19069, the primers exon12F (5'-TTCTACTTGAGCATGTACA-GGG-3') (SEQ ID NO: 3) and exon12R (5'-CTCTCCT-GCTCAGCTATCATC3)) (SEQ ID NO: 4) were used to amplify a 589-bp fragment.

The PCR products were digested with the restriction enzyme MSPAII at 37° C. then electrophoresed on a 2.0% agarose gel. The A allele (cut) was indicated by the 384- and 205-bp fragments, and the G allele (uncut) was indicated by a single 589-bp fragment. For genotyping SNP25402, the primers intron19F (5'-AACTATGTTACTTGTGGCCC 3') (SEQ ID NO: 5) and intron19R (5'-AACAGATCACCAG-GCTCTCC-3') (SEQ ID NO: 6) were used to amplify a 514-bp fragment. The PCR products were digested with the restriction enzyme Hinf1 which allows one to distinguish allele A (514-bp fragment) and allele C (167-bp and 347-bp fragments) when electrophoresed on a 2.0% agarose gel. STAT1 SNP (on chromosome 29) discovery and genotyping was as described in Cobanoglu et al. (2006). Allele frequencies of SNP were calculated by counting numbers of respective alleles in the study sample. Hardy-Weinberg equilibrium (HWE) was tested by Chi-square test.

Statistical Analysis

To test associations between ovary genotypes for the STAT1 and STAT3 SNPs and fertilization rate of oocytes or survival rate of embryos, a generalized linear model for binary response was fitted using the 'logit' link function (McCullagh and Nelder, 1989). The linear combination of predictors can be written as $$\eta_1 = b_0 + \text{bull} + STAT5A + \text{Ovary Genotype}$$

where $b_0$ is a constant term, bull is the effect of the semen used to fertilize the oocytes, STAT5A is the effect of the ovary genotype of a STAT5A SNP that was found to be associated with fertilization rate and embryonic survival rate in a previous study (Khatib et al., 2008a), and Ovary Genotype is the effect of the ovary genotype of the SNP being tested. The response variable is coded as '0' for unsuccessful fertilization/degenerate embryo or '1' for successful fertilization/normal embryo. These two traits were modeled for each of the three SNPs (STAT1 SNP, STAT3 SNP25402 and STAT3 SNP19069) individually. Associations were tested using a Likelihood Ratio Test (LRT) by comparing the above model to a reduced model missing the Ovary Genotype predictor, which tested whether ovary genotype has an effect on fertilization success of oocytes or survival of embryos. LRT statistic is approximately distributed as $\chi_v^2$ with v degrees of freedom that is equal to the difference in numbers of parameters of the two nested models compared. When sample size is large, this approximation is quite accurate (McCullagh and Nelder, 1989). 95% confidence intervals for odds ratios between genotypes were calculated based on estimates and standard errors of the Genotype term in fitted models. The most frequent homozygotes were set as reference and had odds ratios of one. In addition, because of their biological interactions, 2-way interactions between the SNPs were also tested as described previously (Khatib et al., 2009). Briefly, a model including both SNPs and their interaction $$\eta_2 = b_0 + \text{bull} + STAT5A + \text{Genotype1} + \text{Genotype2} + \text{Genotype1:Genotype2}$$

was compared with a reduced model missing the Genotype1:Genotype2 term by LRT. This test was performed for each of the three interactions STAT1:SNP25402, STAT1:SNP19069 and SNP25402:SNP19069. Significant 2-way interactions indicate that the genotype effect of one SNP depends on the genotype of the interacting SNP. Therefore, fertilization or embryonic survival rates were calculated for each of the 9 genotype combinations for statistically significant interactions. Statistical analysis was performed using 'glm' function in R (R Development Core Team, 2008) version 2.8.1 and statistical significance was claimed at the 0.01 level.

Results

In this study we investigated the effects of three SNPs in the STAT1 and STAT3 genes and their interactions on fertility traits in Holstein cattle. In order to mimic pregnancy evaluation in live cows, we have constructed an IVF system which enables us to evaluate fertilization success and early embryonic survival, 2 initial components of pregnancy. We show that interactions between SNPs in the STAT3 gene and interactions between the STAT1 and STAT3 genes contribute significantly to the phenotypic variation in embryonic survival in cattle.

TABLE 1

Minor allele frequency (MAF) and Hardy-Weinberg-Equilibrium (HWE) test of SNPs

| Gene/SNP | Alleles | MAF | HWE (p value) |
| --- | --- | --- | --- |
| STAT3/SNP19069 | A/G | 0.475 | 0.566 |
| STAT3/SNP25402 | A/C | 0.423 | 2.04E−07 |
| STAT1 | C/T | 0.298 | 0.410 |

Table 1 shows minor allele frequencies and tests for HWE of the three SNPs. Only STAT3/SNP25402 showed strong evidence of disequilibrium. Table 2 shows the number of oocytes, fertilization rate, number of embryos and survival rate for the genotypic classes of STAT1 and STAT3 SNP. Single SNP analysis revealed statistically significant association (P=2.502E-05) between SNP25402 in STAT3 and fertilization rate. Oocytes collected from genotype AA ovaries showed 70.1% fertilization rate vs. 66.6% (odds ratio (OR)=0.83 as compared to AA) and 66.3% (OR=0.70) for oocytes collected from AC and CC ovaries, respectively (Table 2). Genotypes of SNP19069 in STAT3 and the STAT1 SNP showed moderate differences in fertilization rate (P=0.016 and P=0.014 respectively). For embryonic survival rate, only SNP19069 showed slight difference between STAT3 genotypes (P=0.010).

In order to quantify the contribution of the interaction between SNP of STAT3 and STAT1, a reduced model with bull and genotype information was compared with a full model including the interactions between SNP (Khatib et al., 2009). The interaction between STAT3 SNP (SNP19069/SNP25402) was highly significant for survival rate (P=3.690E-06) but not for fertilization rate. Also, the interaction between STAT1 SNP and SNP19069 was highly significant for survival rate (P=0.422E-06).

TABLE 2

Number of oocytes, fertilization rate (±SEM), number of embryos, survival rate (±SEM), and odds ratios for genotypic classes of STAT1 and STAT3

| Gene/SNP | Genotype (No. of ovaries) | No. of oocytes | Fertilization rate ± SEM | Odds Ratio[1] (95% CI) | No. of embryos | Survival rate ± SEM | Odds Ratio (95% CI) |
|---|---|---|---|---|---|---|---|
| STAT3/ | AA (119) | 2,119 | 0.683 ± 0.010 | 1 | 1,448 | 0.353 ± 0.012 | 1 |
| SNP19069 | AG (229) | 3,734 | 0.674 ± 0.008 | [0.82, 1.05] | 2,518 | 0.328 ± 0.009 | [0.72, 0.96] |
|  | GG (97) | 1,641 | 0.662 ± 0.012 | [0.68, 0.93] | 1,086 | 0.330 ± 0.014 | [0.63, 0.92] |
| STAT3/ | AA (169) | 2,772 | 0.701 ± 0.009 | 1 | 1,942 | 0.329 ± 0.011 | 1 |
| SNP25402 | AC (155) | 2,697 | 0.666 ± 0.009 | [0.74, 0.94] | 1,795 | 0.327 ± 0.011 | [0.84, 1.13] |
|  | CC (103) | 1,852 | 0.663 ± 0.011 | [0.60, 0.82] | 1,228 | 0.365 ± 0.014 | [0.88, 1.26] |
| STAT1 | CC (214) | 3,538 | 0.688 ± 0.008 | 1 | 2,435 | 0.331 ± 0.009 | 1 |
|  | CT (193) | 3,441 | 0.663 ± 0.008 | [0.78, 0.96] | 2,282 | 0.334 ± 0.010 | [0.85, 1.10] |
|  | TT (35) | 540 | 0.663 ± 0.020 | [0.70, 1.04] | 358 | 0.380 ± 0.026 | [0.92, 1.48] |

[1]Odds ratios of the most frequent homozygotes were set to one as a reference

For significant interactions, we calculated the observed embryonic survival rates for each genotype combination of the 2-way interactions. As expected for a statistically significant interaction, genotypic effects of one SNP were dependent on the genotype of the interacting SNP. For example, for SNP25402/SNP19069 interaction, the survival rate of embryos produced from ovaries with AA genotype for SNP19069 (0.399) was markedly higher than that of embryos produced from GG ovaries (0.312), only when the genotype of SNP25402 was AC (Table 3). Embryos produced from AA/GG oocytes showed an extremely reduced survival rate (0.067) compared to all other genotypic combinations. However, it is worth noting that only 75 embryos carry the AA/GG combination. For the STAT1/SNP19069 interaction, the observed survival rate was 0.268 for embryos produced from TT/GG ovaries and 0.394 for embryos produced from TT/AG ovaries, yet this difference between GG and AG ovaries was reversed when STAT1 genotype was CC (0.368 vs 0.319). Taken together, these results strongly suggest a clear genetic interaction (epistasis) between genes that interact biologically.

TABLE 3

Observed survival rates (±SEM), numbers of embryos and average numbers of embryos per ovary for genotype combinations of SNP25402 and SNP19069

| SNP25402/ SNP19069 | AA ($n^1$, $n^2$) | AG | GG |
|---|---|---|---|
| AA | 0.338 ± 0.014 (1097, 12.0) | 0.343 ± 0.017 (747, 11.5) | 0.067 ± 0.029 (75, 6.8) |
| AC | 0.339 ± 0.033 (218, 14.5) | 0.312 ± 0.012 (1367, 11.1) | 0.325 ± 0.034 (188, 11.8) |
| CC | 0.627 ± 0.063 (59, 14.8) | 0.346 ± 0.026 (338, 11.6) | 0.359 ± 0.017 (786, 11.9) |

$n^1$ = Number of embryos
$n^2$ = Average number of embryos per ovary

TABLE 4

Observed survival rates (±SEM), numbers of embryos and average numbers of embryos per ovary for genotype combinations of STAT1 SNP and SNP19069

| STAT1/ SNP19069 | AA ($n^1$, $n^2$) | AG | GG |
|---|---|---|---|
| CC | 0.327 ± 0.019 (587, 11.1) | 0.319 ± 0.013 (1261, 11.1) | 0.368 ± 0.020 (549, 12.5) |
| CT | 0.361 ± 0.018 (753, 13.4) | 0.328 ± 0.014 (1037, 11.3) | 0.295 ± 0.022 (440, 10.7) |
| TT | 0.508 ± 0.063 (63, 12.6) | 0.394 ± 0.035 (198, 11.0) | 0.269 ± 0.045 (97, 8.1) |

[1]Number of embryos
[2]Average number of embryos per ovary

While the invention has been described in connection with one or more embodiments, it should be understood that the invention is not limited to those embodiments, and the description is intended to cover all alternatives, modifications, and equivalents, as may be included within the spirit and scope of the appended claims.

REFERENCES CITED

Carlborg, O., and C. S. Haley. 2004. Epistasis: too often neglected in complex trait studies? Nat. Rev. Genet. 5:618-625.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89:4433-4437.

Darnell, J. E. 1997. STATs and gene regulation. Science 277:1630-1635.

Dobson, H., S. L. Walker, M. J. Morris, J. E. Routly, and R. F. Smith. 2008. Why is it getting more difficult to successfully artificially inseminate dairy cows? Animal 2:1104-1111.

Hombria, J. C. and S. Brown. 2002. The fertile field of Drosophila Jak/STAT signaling. Curr. Biol. 12:R569-R575.

Kisseleva, T., S. Bhattacharya, J. Braunstein and C. W. Schindler. 2002. Signaling through the JAK/STAT pathway, recent advances and future challenges. Gene 285:1-24.

Khatib, H., R. L. Monson, V. Schutzkus, D. M. Kohl, G. J. Rosa, and J. J. Rutledge. 2008a. Mutations in the STAT5A gene are associated with embryonic survival and milk composition in cattle. J. Dairy Sci. 91:784-793.

Khatib, H., C. Maltecca, R. L. Monson, V. Schutzkus, X. Wang, and J. J. Rutledge. 2008b. The fibroblast growth factor 2 gene is associated with embryonic mortality in cattle. J. Anim. Sci. 86:2063-2067.

Khatib, H., W. Huang, X. Wang, A. H. Tran, A. B. Bindrim, V. Schutzkus, R. L. Monson, and B. S. Yandell. 2009. Single gene and gene interaction effects on fertilization and embryonic survival rates in cattle. J. Dairy Sci. 92:2238-2247.

Kodama, H., K. Fukuda, J. Pan, S. Makino, A. Baba, S. Hori, and S. Ogawa. 1997. Leukemia inhibitory factor, a potent cardiac hypertrophic cytokine, activates the JAK/STAT pathway in rat cardiomyocytes. Circ. Res. 81:656-663.

Maj, T., and A. Chelmonska-Soyta. 2007. Pleiotropy and redundancy of STAT proteins in early pregnancy. Reprod. Domest. Anim. 42:343-353.

McCullagh, P., and J. A. Nelder. 1989. Generalized Linear Models, 2nd edn. Chapman and Hall, London.

Morris, D., and M. Diskin. 2008. Effect of progesterone on embryo survival. Animal 2:1112-1119.

R Development Core Team. 2008. R: A Language and Environment for Statistical Computing. R Foundation for Statistical Computing, Vienna, Austria. (www.R-project.org).

Royal, M., G. E. Mann, and A. P. Flint. 2000. Strategies for reversing the trend towards subfertility in dairy cattle. Vet. J. 160:53-60.

Santos, J. E. P., W. W. Thatcher, R. C. Chebel, R. L. A. Cerri, and K. N. Galvao. 2004. The effect of embryonic death rates in cattle on the efficacy of estrus synchronization programs. Anim. Reprod. Sci. 83:513-535.

Shook G. E. 2006. Major advances in determining appropriate selection goals. J. Dairy Sci. 89:1349-1361.

Takeda, K., K. Noguchi, W. Shi, T. Tanaka, M. Matsumoto, N. Yoshida, T. Kishimoto, and S. Akira. 1997. Targeted disruption of the mouse Stat3 gene leads to early embryonic lethality. Proc. Natl. Acad. Sci. USA. 94:3801-3804.

Teglund, S., C. McKay, E. Schuetz, J. M. van Deursen, D. Stravopodis, D. Wang, M. Brown, S. Bodner, G. Grosveld and J. N. Ihle. 1998. Stat5a and Stat5b proteins have essential and nonessential, or redundant, roles in cytokine responses. Cell 93:841-850.

Truchet, S., M. Chebrout, C. Djediat, J. Wietzerbin, and P. Debey. 2004. Presence of permanently activated signal transducers and activators of transcription in nuclear interchromatin granules of unstimulated mouse oocytes and preimplantation embryos. Biol. Reprod. 71:1330-1339.

VanRaden, P. M., A. H. Sanders, M. E. Tooker, R. H. Miller, H. D. Norman, M. T. Kuhn, and G. R. Wiggans. 2004. Development of a national genetic evaluation for cow fertility. J. Dairy Sci. 87:2285-2292.

What is claimed is:

1. A dairy cattle breeding method, the method comprising: obtaining a genomic DNA sample of a dairy cattle animal, detecting in the genomic DNA sample in STAT3 gene, wherein the genotype comprises AA or AG at position 1009, or AA or AC at position 7342 corresponding to SEQ ID NO:1 respectively, and using a cell from the animal in a breeding process.

2. The method according to claim 1, further comprising detecting the presence in a STAT1 gene, wherein the genotype comprises CC or CT at position 213 of SEQ ID NO:2, and using a cell from the animal in a breeding process.

3. A method for selectively breeding a dairy cattle animal, the method comprising: obtaining a genomic DNA sample from the animal, detecting in the genomic DNA a genotype in a STAT3 gene and a STAT1 gene, wherein the genotype of STAT3 gene comprises AA or AG at position 1009 corresponding to SEQ ID NO:1 and the genotype of STAT1 gene comprises CC or CT at position 213 of SEQ ID NO:2, and using a cell from the animal in a breeding process.

4. The method according to claim 1, wherein detecting the genotype is performed by sequencing.

5. The method according to claim 2, wherein the genomic DNA sample is from an embryo.

6. The method according to claim 5, wherein detecting the genotype is performed by sequencing.

7. The method according to claim 3, wherein detecting the genotype is performed by sequencing.

8. The method according to claim 1, wherein an in vitro fertilization method is used.

9. The method according to claim 8, wherein the cell is an egg from a superovulating female animal.

10. The method according to claim 9, wherein a MOET procedure is used.

11. The method according to claim 1, wherein the cell is a sperm from a bull animal.

12. The method according to claim 2, wherein an in vitro fertilization method is used.

13. The method according to claim 12, wherein the cell is an egg from a superovulating female animal.

14. The method according to claim 13, wherein a MOET procedure is used.

15. The method according to claim 2, wherein the cell is a sperm from a bull animal.

16. The method according to claim 3, wherein an in vitro fertilization method is used.

17. The method according to claim 16, wherein the cell is an egg from a superovulating female animal.

18. The method according to claim 17, wherein a MOET procedure is used.

19. The method according to claim 3, wherein the cell is a sperm from a bull animal.

* * * * *

SEQUENCE LISTING

```
<160> NUMBER OF SEQ ID NOS: 6

<210> SEQ ID NO 1
<211> LENGTH: 8400
<212> TYPE: DNA
<213> ORGANISM: Bos taurus

<400> SEQUENCE: 1
acttttaaaa cagtactaaa ataatgttaa caagaaaaca ctgagaaatg gtgactatgt      60
aaaaaatgaa atactcaaaa acagttaaag gacaaggaac atgctgggaa gaatttttct     120
ggcgatgtca atgggatact ctgagttgca ggtaacagta gacctttaca gaaagcccag     180
tgtggcttca gtaataagga aatttgcaac ccagtataac tggaaatgca gttagaacaa     240
gttccgggtg gtgaaatcag tgactcaatt cctgtcacca aggatccaga accttccgtc     300
tctcttctct gccaccataa gtagcacggg cattcgaggg ttccctctgg ttgcagcatg     360
gttgcttgta gtaaaggcca cgtgtctcct tgctgatgtg cagctgaagc tacagaatgt     420
aaatccagcc tgagggagaa ttccttcccc gtcggattga gacagtgtgg gtcctggcct     480
cactcctgga ccaacactgt gcacatgctc ggttctgtgg gcttagagca ggatcccctg     540
gaagtgggga tgggaaagat acttgctgga gtcaaggttc tgttaggaag aggggagtag     600
aggttgggta ggcaaccagc tgtgtcttct acttgagcat gtacagggat gttagatttc     660
acgtatacca tgtaatcgag tccttgacag aaatccccag gagaacagca gtttttccat     720
ccgagtaaat gataggtgtt caaagtggac tttcaaagag actcggggcc tgtttttatta    780 acactggttt atattcttaa cagagactcc ggggacgttg cagctctcag agggtaagtt     840
cagcatacag gcttccttct gttctgtata atctaacttt gtccctggcc attcggtcac     900
gtatgtggtt ggtctttttcc tcctgtgatt caggtcccgg aaatttaaca ttctgggcac     960
aaacacgaaa gtgatgaaca tggaagagtc taacaatggc agcctctcag cggagttcaa    1020
acacttggta catgggagaa gcctgggctc cctttctgca gggcctctgg caggggagg      1080
```

```
gacttgggga gagccttacc tgacggagga tgctctttgt ttttcttaca gaccctgaga    1140
gagcagagat gcggtaatgg gggccgagcc aattgtgatg taagttttgt tggagatgat    1200
agctgagcag gagagaaaaa gagcctccat aagaacttcc ctagtggtta agactccacg    1260
cttccaatgc aggggtgtg ggtttgatcc ctggttagag aactaagatc tcacatgcct    1320
tgcagccaaa acactgaaac tttttataaa aagaaagaa aaagagcctc cttactgccc    1380
agaagtagag acacctacct gctatttcag ctgcagtcac cgccagccaa cacatgagta    1440
gtcacacatg ccttggagga gttctctggc tcagcgcatt tccttgattg tccggagagt    1500
tagctcatct ttaaggagtg taaagtccct tgcccacacc catttggtag aaaaggagcc    1560
ttccgccttg cctgggactt tccaaattcc ccttctaact tctatgcact gacacggctt    1620
gtctcagctt ttggtgatct gttttggtca ctgaggtggg atgggtttca acacatccaa    1680
gttaaacatt ttaccaaaag agaaacagca aactctcttg ttctttaccc accttgtttc    1740
ttctctgtct cccattgact cagattcttg gattcttagt gttaagaata aacttaaggg    1800
aattccttgg tgattcagtg gttaagactc caggccttca ctgccatggg cctgggttca    1860
attcctggtt gggaaactaa gattccacaa actatatggc cccccaaaaa agaataaact    1920
ttaaaaaaga gaaagtatat gtgaccaagc actggtttta aatcttttttt ataaaattgt    1980 gacaccctat tcttttttctg tttgtctcct gagccgttct taccctcttc tctagaatgt    2040
agcaggcctt ttaaaaaaac aaactgaatc tataagactt gacagcagtt aaagagtgag    2100
gttgtttcta tgcagtgata tgggaagatg tatgtggcat atttattgag aaaaaaatgc    2160
aaagtaattt gagtagtata ctagtataat tgttttaaaa tttactgttt tttctccatt    2220
catgtctgca ttacaaaatt ctagaggaat gtctaccaaa tagtgcttat atatttgtgc    2280
tgctgttctc acccaaagct actctatact atctctgtaa tatttgcatt taaaattgaa    2340
tgtgtatttc ttttgttatg agagaacatt ttaaaatatg agttggaatt tctaataatt    2400
cattgacagt tctcattcaa aatagtcgct atgttgctgg tgtatcaatt gttataatca    2460
ctttgaaaaa cagttgggca ttatgaaaat aaatataccc tatataccag cagtgccact    2520
ctcgggattt aacaatagag aaatctttgc tcataggtgc caggagactg gcgccaggag    2580
acatgcattt catgtcccaa cagcctaatt gtaaggccta aatacaaccc atatgtcaac    2640
agcactagag tggataaatg atctgtggta tagtcaggtg atggaatact atacagctat    2700
gaagatgtat aaattgcagg tatacacaat tacataggtg tgaaaagcga gtcacagtat    2760
gagattcaca accccacccc caaattaaac aacacataca ttgtttagag atataaatgc    2820
aggaaaacca taaagaaggg ctaggaaatg acaaactcaa aagacaaaat agcagtcact    2880
tctgaggtag gaggctcagg gatggatgga gttgggaagg gcacccggag aacctccatg    2940
gtgacggtct ctgccttaca ctgaggggtg ggtacacagg tgttcagtct tttgccatta    3000
tgctgttccc atttttatcca tgaccaactg gatctcccata gtcatcataat aaagccgata    3060 agaggtcagg ttgtagatca gagcactgga gagtcgtaga gttggaaaga ccatgtgctc    3120
cagttgtatc catggccacc tggtgcgttg cgcttcagga tggtgtagtg atggctgtca    3180
ggactcagtg ccatcctctc tgaggaagag catccttctc attctcgtag gcctccctga    3240
ttgtgaccga ggagctgcac ctgatcacct ttgagactga ggtgtatcac caaggcctca    3300
agattgacct ggaggtgagt tctgcacaga actgggtaga accgcctgca ggatgattca    3360
gaatggggct tcttctagtc agggttttca ctctagaagg tggaatgatg actctttact    3420
```

```
cagcactgtg tttacatttg cttcttttc tccaaaaatt tgttagtatc ttgcctgagt    3480
gcttagaaga tacatgtcta ctcaggttcc agcgaacttg atgtaaaaac tcgtatttag    3540
gaattaatta tagccaactt tatacagttt ggacaaaaca gtctttcaac caccaccgtt    3600
tttagtatcc aaacaatcat ggcatttacc tgctctttcc ccaactttct tgattttaaa    3660
ttaaagatac acctgaaaaa gcaagcaccc tagtctttga ttcctgggac ctctctatta    3720
aatgggcaga tacagcttca atgcagcaat gcgggagact tgggttcgac ttccctgggt    3780
tggaaagatc ccctggagaa gggaaaggct acccactcca gtatcctggc ctggagaatt    3840
ccacggactg tataggccat ggggtcgcag agttggacac aactgagcaa cttgcattct    3900
tttcacagct tcaattcgtg aaagtcttcc aagttttata atgggagt ccgtggactg    3960 tgagtccact gtgaggagtc agcttttgtaa attcctggtg atactcagac agcccctgag    4020
ttcagcctac tctccacgct gggtgtcaag ctgaccgggc cccacagctt cctgagggtt    4080
ggcagcaagt gtactccacg acctctcctt ttattctgaa ccctgcgaga tgcgggtgaa    4140
gaggtttctg gagcctcaag ggccctctgc ctccccagct cattccccgc tccctccaca    4200
gacccactcc ttgccagtgg tggtgatctc caacatctgt cagatgccca atgcctgggc    4260
gtccatccta tggtacaaca tgctgaccaa caaccccaag gtgagttgga ggcccgggtt    4320
ctccggaggc tccttggtgc ctcggggctg ccgcccagca ggcgccaccc tctcatctaa    4380
aggagcaaat gtgtcatttc caatagaacg tgaactttt caccaaaccc ccgatcggaa    4440
cgtgggatca agtggccgag gtgctgagct ggcagttctc ctctaccacc aagcgcgggc    4500
tgagcatcga gcagttgacg acgctggcgg agaaactctt aggtcagccc ttgacctctt    4560
ctccctttgc tgtccttgca aaaggaatct ggcccatggg gttgttcgtt gaggaaagtt    4620
gactgagcaa ggcgctgggc agaatacacg tgctccagca ggccctgaaa tcgggacgca    4680
gaggaggttt gcgcctgtga tcacttttat gagacgggag gcagatttct tctgttggtg    4740
gctgtctccc tgggtacttt gtccagcctt aggaaagtat tttaaatgta tgttcgagct    4800
aaaggcttgg catccctgtc tgtttttttca agaaaatgta gcttgttttt aatttttttt    4860
cctggaagaa aaaagtctta gaatgttttta cgtgccgtct agctttgtcc tgtgctgcca    4920
tgaaacatgg gctctccggg tgcctcagtg gtagagaatc cacctgccag tgcaggagac    4980
ttggatttga cccttgggtc aggaagatcc cctggaggag gaaatgataa cccactccag    5040
tattcttgcc tgggaaatcc caaggagagg aacttggtag ggctgcagtc agacatgact    5100
gagggactga ccatgcatga ctaaacgtga ccctgtaact caagctgtca gcttcttagt    5160
gtgttctgct gatccccaga ctgccacacg aggctagaaa gggcagcagg gacttgatac    5220
atcacccacc acctccgcta acaacaact taggggcat caaacgatgg gattgggtgg    5280
tggggagggg tgcgtatgta tgcacacaag agtgccaacg ttcaagtgca tgaaaaccaa    5340
gtttcggggc gtgttgtggg acaactgtct gtctgtctgt ttgaagaaag atctggattt    5400
aaaactgcaa attatatgac ttttttttt ctttcaggac ctggtgtgaa ctattcaggg    5460
tgtcagatca catgggctaa attttgcaaa gtaagccacc gtgtgaactc catccatgag    5520
gctgcctcat aggaggagga gggggcaggg acacttagct gtggggatgt cgtggagggc    5580
agtgggcctg aaggccccgg actcttggtc tggcggccaa gatgacctgc ctgagggtag    5640
atgggcttga ggattttggt ggcacctcac ccccttaaag gaagagccca gggaggtggg    5700
ggactgacct ttcccattac tcttttctcc aggaaaacat ggctggcaag ggcttctcct    5760
tctgggtctg gctggacaac atcattgacc tggtgaaaaa gtacatcctg gccctttgga    5820
```

-continued

```
acgaagggta ggttggaact cttgtgtctg acagaacaca cagggtgac aagtcgccta    5880
ctctcccagc aggttggctg caacacagag gtccctcagc cccaaccttg ctgttgctcc    5940
tctctgtctc caggtatata atgggcttca tcagcaagga gagggaacgg gccatcttga    6000
gcactaagcc cccaggtacc ttcctgctga gattcagtga aagcagcaaa gaaggaggcg    6060
tcaccttcac ctgggtggag aaggacatca gcggtaagct tagtgattcc ccaccgcaac    6120
ttgtggccag cactgctgtg gctggccatg gctgctgcta gtttcaggca cctgctgccc    6180
ccttgtgggc agggatggcc tcgcattctc ctgcctcaga cttggaaggt acccggtgat    6240
cattttatg agatgggaag acttggcttc tctaaattct tccagctgga ggattggttt    6300
gccagtttta ttttgctccc tgcaaggggt taatcagttc agtcgctcag tcgtgtccga    6360
ctctttgtga cccatgagt cacagcacgc caggcctccc tgtcatcacc aactcccaga    6420
gttcactcaa actcatgtcc atcgagtcag tgatgtcatc cagccatctc atcctctgtc    6480
gtccccttct cctcctgccc ccaatccctc ccagcatcag ggtctttcc aatgagtcaa    6540
ctctttgcat gaggtggcca agtaatgga gtttcagctt tagcatcagt ccttccaatg    6600
aacacccagg actgatctcc tttaggatgg actggttgga cctccttgca gtccaaggga    6660
ctctcaagag tcttctccaa taccacagtt caaaagtatc aattctttgg cgctcagctt    6720
tcttcacagt ccaactctcg catccataca tgaccactgg aaaaaccata tccttgacta    6780
gacggaccct tgttggcaaa gtaatgtctc tgcttttgag tatgctatct aggttggtca    6840
taactttcct tccaaggagt aagcgtcttt taatttcatg gctgcagtca ccatctgcag    6900
tgattttgag ccccccaaaa taaagtctga cactgtttcc actgctgccc catctatttg    6960
ccatgaagtg atgggaccgg atgccatgat cttcattttc tgaatgttga gctttaagcc    7020
aactttttca ctctcctctt tcactttctt caagaggcta atatttgcct agaaaattggt    7080
aattttttt tttgaaattt gaatttaaa ttgtattctt catctccttt cttacccact    7140
ctgttcatat atcttataaa agtaattatt caactatgtt acttgtggcc cagctgaata    7200
gcttctcccg aagcctgctg aacatttcca tagtaccaga caactgggca gaatattcag    7260
ggtctcgaac actaggttgg cataagccctt tcccccctcaa gggaaaatca atcaggtagt    7320
cttctctaag atcacccgag tattctcttt ctgtatccca tgacaggcaa gacccagatc    7380
cagtcagtgg aaccttacac caagcagcag ctgaacaaca tgtcatttgc tgaaataatc    7440
atgggctata agatcatgga tgccaccaat atcctggtgt ctccactggt ctatctctac    7500
cccgacattc aaaggagga gcgttcgga agtactgtc ggccggagag ccaggagcat    7560
cctgaagccg acccaggtag ttgttgattt tccgcaacag ccacttggtt ctggggagaa    7620
gtgggaaatc gtaggatcct tgggggacag gtaaggtaaa tgcctggaga gcctggtgat    7680
ctgttttttt ctttctttct ttttaagaaa ttttctcttt ataattttta tttatttatt    7740
tttgttttg gctgtgctgg gtcttcattg ccgtatgggc ttttctgtag ttggggcaag    7800
cgggggctat gctctacttg cagtgcgtgg gcttctcatt gcggtggctt ctcttgttgc    7860
agagcttggg ctctaggcac agacttcagt agttgcggca ggtgggctca gtagttgcag    7920
ttcccaggct ctagagccac aggctcaatg gttgtggcac acgggcttag ttactccgag    7980
gcatatggag tcttctcgga ccagggatca aacctgtgtc tcctgcgttg gcaggcaaat    8040
tctttaccac cgagatatcc aggaaagccc agtctggtga tctttattcc tctttctggg    8100
aaagaactta atagtgagtg cctttagggg caattgatgg ggttagagag aggagaggaa    8160
```

```
tcagtcacca ggctctgccc cactggaggc accggtctaa aggggaaaac agctcacaca    8220
tacccagaca tacctaagac actacgaaga gaaaccgagg gcggaattct ctagaaacag    8280
gatgcccagc cagcacagca cttcttgcaa agcatatgct ggaaggtttg cgactcagac    8340
ttcagtctag agtgtttcct ttccccatca ttgaacaatg taagcagccc aagtgggatg    8400
```

<210> SEQ ID NO 2
<211> LENGTH: 626
<212> TYPE: DNA
<213> ORGANISM: Bos taurus

<400> SEQUENCE: 2

```
ctttaaatat agcctcaagt ttgccagtgg cttgcctgtg aaatagtgca aagctgtcct      60
gtatctgggc agaggataaa agttatgtgt gttattatat tttccacact ggccattgaa     120
aactaaagat tctctttctt gggagaatta gcttttggta tggctttatg atgctggcta     180
atatcaatag aaggaagtaa acttttacaaa ttcatgagta gtatcttcca tttcagcttt    240
aataccaaag ttgaatatat tctgccttca tcatgaaatt gaagttagta aatgaaactg     300
tcttcacagt tctatcaagg gagccaaact attaacagct ctcttaaggc aaatcctatt     360 atttttttcaa aaagttgaaa ttaattgtag atgtaaacaa actcagaaat ttaatgcatg    420
tttcataagt gggttcactt gtctttattg tttagtaaaa attttaaaat tgagaagaaa     480
aactagtaat tgacaaatca ttaggtggag attatgagaa tccaataatt tgaaaactca     540
tcctgtgtaa ctgccttgag aattgggtaa ttttcactgg caaatgtgta tctctcacaa     600
atacattaca gatggttcca ctaaaa                                          626
```

<210> SEQ ID NO 3
<211> LENGTH: 22
<212> TYPE: DNA
<213> ORGANISM: Artificial Sequence
<220> FEATURE:
<223> OTHER INFORMATION: Primer exon12F

<400> SEQUENCE: 3

```
ttctacttga gcatgtacag gg                                               22
```

<210> SEQ ID NO 4
<211> LENGTH: 21
<212> TYPE: DNA
<213> ORGANISM: Artificial Sequence
<220> FEATURE:
<223> OTHER INFORMATION: Primer exon12R

<400> SEQUENCE: 4

```
ctctcctgct cagctatcat c                                                21
```

<210> SEQ ID NO 5
<211> LENGTH: 20
<212> TYPE: DNA
<213> ORGANISM: Artificial Sequence
<220> FEATURE:
<223> OTHER INFORMATION: Primer intron19F

<400> SEQUENCE: 5

```
aactatgtta cttgtggccc                                                  20
```

<210> SEQ ID NO 6
<211> LENGTH: 20
<212> TYPE: DNA
<213> ORGANISM: Artificial Sequence -continued

```
<220> FEATURE:
<223> OTHER INFORMATION: Primer intron19R

<400> SEQUENCE: 6
aacagatcac caggctctcc                                               20
```